United States Patent [19]

Chen et al.

[11] 4,078,552
[45] Mar. 14, 1978

[54] DEVICE FOR AND METHOD OF MAKING STANDARD AND REPRODUCIBLE SKIN PUNCTURES

[75] Inventors: Evan N. Chen, Fairfield, Conn.; Arthur L. Babson, Chester, N.J.

[73] Assignee: Warner-Lambert Company, Morris Plains, N.J.

[21] Appl. No.: 589,227

[22] Filed: Jun. 23, 1975

[51] Int. Cl.² .................... A61B 5/02; A61B 17/32
[52] U.S. Cl. ..................................... 128/2 G; 128/314
[58] Field of Search ............... 30/272 R, 273, 286, 30/299; 128/305, 314, 2 G

[56] References Cited

U.S. PATENT DOCUMENTS

| 55,620 | 6/1876 | Capewell | 128/314 |
|---|---|---|---|
| 361,533 | 4/1887 | Little | 128/314 |
| 580,969 | 4/1897 | Cohn | 30/272 R |
| 1,260,827 | 3/1918 | Stefanov | 30/272 R X |
| 1,572,191 | 2/1926 | Donnelly | 30/299 X |
| 2,711,738 | 6/1955 | Kelly et al. | 128/314 |
| 3,030,959 | 4/1962 | Grünert | 128/314 X |
| 3,712,293 | 1/1973 | Mielke, Jr. | 128/2 G |
| 3,762,416 | 10/1973 | Moss et al. | 128/305 |

FOREIGN PATENT DOCUMENTS

| 998,838 | 9/1951 | France | 30/299 |

OTHER PUBLICATIONS

Sutor; Anton H. et al., "Bleeding from Standardized Skin Punctures," IN Amer. J. Clin. Path. 55: pp. 541-550, 1971.

*Primary Examiner*—Channing L. Pace
*Attorney, Agent, or Firm*—Albert H. Graddis; Jeremiah J. Duggan

[57] ABSTRACT

The specific disclosure provides a device and method of making an incision of precise dimensions in a patient, preferably in the forearm, and determining exact bleeding from initial puncture of the skin until the flow of blood has ceased, i.e. hemostatis is complete. The device comprises a housing including a blade aperture at one end thereof adapted to be positioned in abutting engagement with the skin of the subject. A spring member and a blade member having at least one cutting edge are located in the housing. Means are also provided in the housing and is connected to the blade member for retracting the blade member inwardly from the blade aperture and against the bias of the spring member. Manually operable means are provided for releasably engaging the retracting means to maintain the blade member in a retracted position against the bias of the spring member until the device is ready for use. The engaging means is manually operable to irretrievably disengage the retracting means, thereby permitting the retracting means and the blade member to move under the bias of the spring member to position the at least one cutting edge a predetermined distance outwardly from the blade aperture.

14 Claims, 6 Drawing Figures

U.S. Patent     March 14, 1978     4,078,552
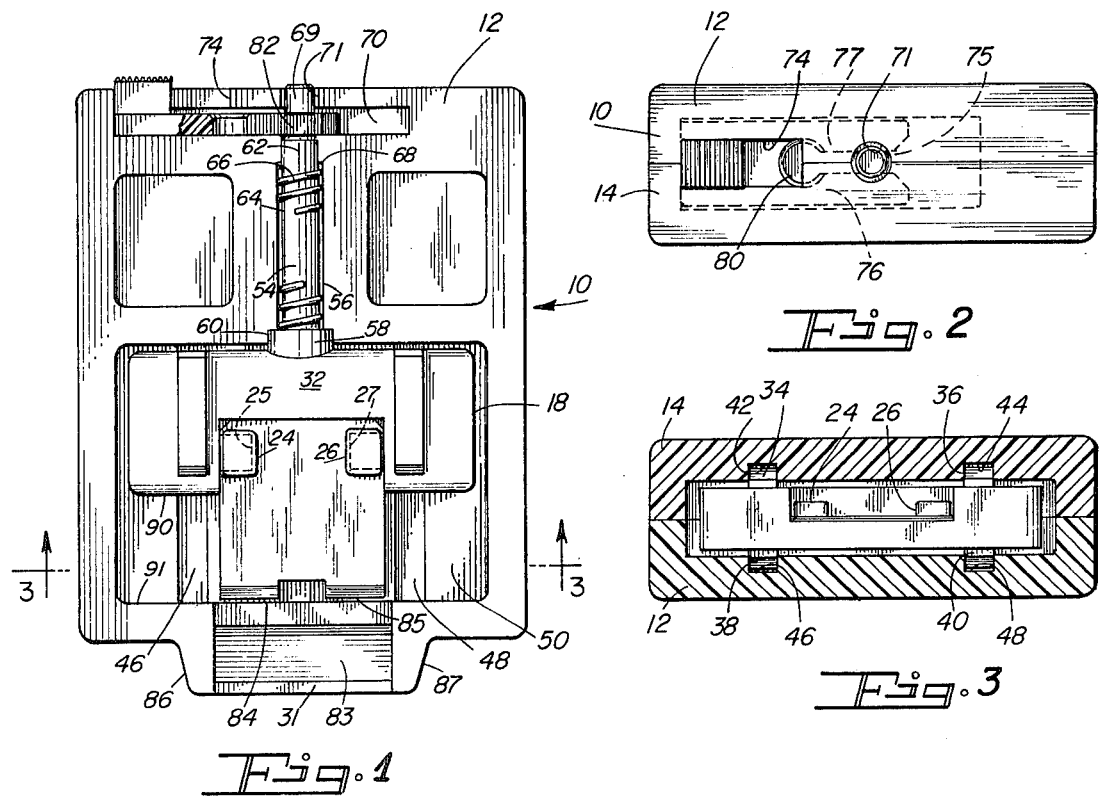
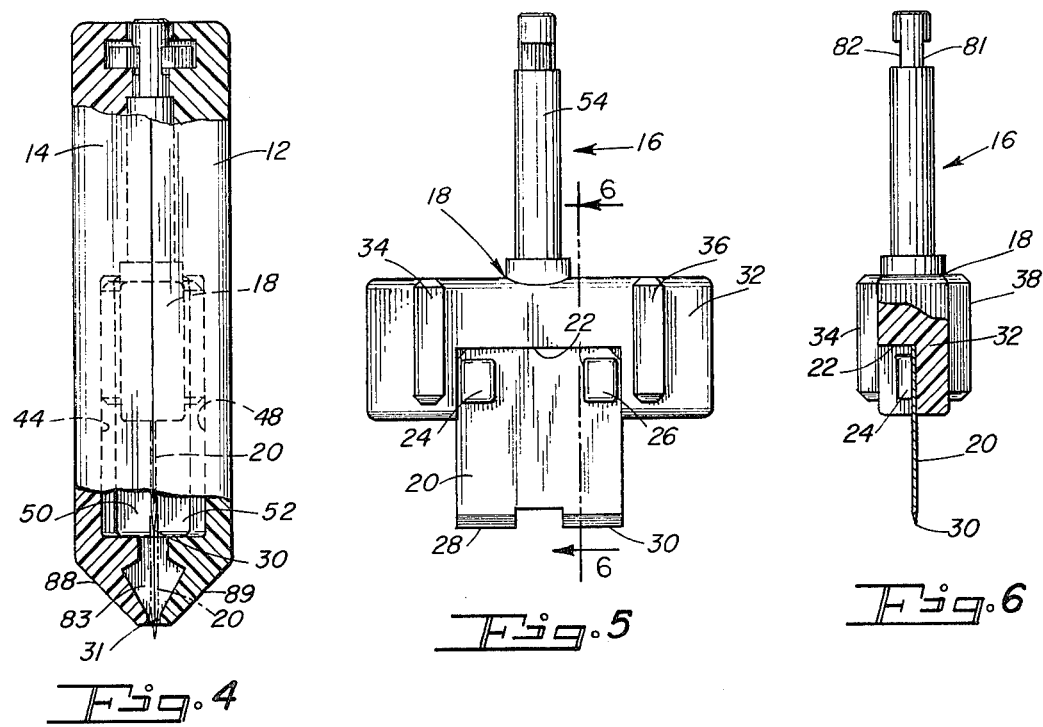

DEVICE FOR AND METHOD OF MAKING STANDARD AND REPRODUCIBLE SKIN PUNCTURES

BACKGROUND OF THE INVENTION

1. Field of the Invention

The present invention relates to a novel method and a disposable device for producing precisely controlled incisions in the skin of a patient to permit observation of the flow of blood from such incisions in accordance with the standard Ivy technique or other methods for the determination of rate of blood loss or bleeding time.

2. Description of the Prior Art

In the past, devices employed for making a standardized reproducible blade incision for bleeding time determinations have included combinations of an incision blade employed together with a template having a blade guide slot such as disclosed in U.S. Pat. No. 3,712,293. Aside from the obvious cumbersomeness, such a two component testing device presents to the operator test equipment which may give rise to faulty results because of the necessity of manual manipulation of the incision blade.

Sutor et al. had described in the American Journal of Clinical Pathology, 55, Pages 541–550 (May 1971) the "Mayo Automatic Lancelot" for use in producing incisions of a predetermined dimension in patients being tested for bleeding time. This device employs a spring loaded plunger which, when released, contacts and drives a spring-restrained rod-like member carrying a Bard-Parker blade a predetermined distance to produce the desired incision. The relatively complex mechanism described by Sutor et al. is clearly not suitable for a disposable device.

SUMMARY OF THE INVENTION

In accordance with the present invention there is provided a device for testing the bleeding time of a human subject comprising a housing including a blade aperture at one end thereof adapted to the positioned in abutting engagement with the skin of the subject. A spring member and a blade member having at least one cutting edge are positioned in the housing. Means in the housing is connected to the blade member for retracting the blade member inwardly from the blade aperture and against the bias of the spring member. Means are provided for releasably engaging the retracting means to maintain the blade member in a retracted position against the bias of the spring member until the device is ready for use. The engaging means is manually operable to irretrievably disengage the retracting means, and thereby permit the retracting means and the blade member to move under the bias of the spring member to position the at least one cutting edge of predetermined distance outwardly from the blade aperture.

The present invention also provides a method for simultaneously providing a plurality of incisions such that the bleeding times for the incisions may be averaged to produce a more accurate bleeding time.

BRIEF DESCRIPTION OF THE DRAWINGS

FIG. 1 is a side elevational view of a device constructed in accordance with the present invention with one side thereof removed;

FIG. 2 is a top plan view of the device of FIG. 1;

FIG. 3 is a cross-sectional view of the device of FIG. 1 taken along lines 3—3 of FIG. 1;

FIG. 4 is a side elevational view of the device of FIG. 1 with portions removed;

FIG. 5 is a side elevational view of a blade holder and a blade member for use in a device of FIG. 1; and FIG. 6 is a cross-sectional view of the blade holder and the blade member taken along lines 6—6 of FIG. 5.

DESCRIPTION OF SPECIFIC EMBODIMENTS

With reference to the figures, a specific embodiment of the present invention provides a device 10 for testing the bleeding time of a human subject by making at least one standard and reproducible skin puncture in a patient, preferably in the forearm, and determining the exact bleeding time from the initial puncture of the skin until the flow of blood has ceased, i.e. hemostatis is complete.

The device 10 has opposing side walls 12, 14 bonded together by any suitable means such as ultrasonic welding, adhesives, and mechanical means such as staking, riveting, etc. An incision blade assembly 16 is vertically movable within the device 10. The incision blade assembly 16 includes a blade holder 18 having an incision blade 20 positioned in a recessed portion 22. In the specific embodiment of the drawings, the blade holder 18 is formed of plastic, and the blade 20 is secured thereto by deforming or staking the outer ends of posts 24, 26 which extend through perforations 25, 27 in the upper end of the blade 20. The blade 20 has a pair of spaced cutting edges 28, 30 at the lower end thereof which are positioned in vertical alignment above a blade aperture 31 formed at the lower end of the device 10. The blade holder 18 has a pair of vertical rails 34, 36; 38, 40 formed on opposite sides of a transverse wall 32. The rails 34–40 are slidably located in vertically grooved recesses 42, 44, 46, 48 formed in opposing hollowed portions 50, 52 of the side walls 12, 14. A post 54 extends upwardly from the transverse wall 32 in a bore 56 formed in the housing defined by the side walls 12, 14. The post 54 has an enlarged diameter lower portion 58 which is seated in a similarly enlarged lower portion 60 of the bore 56 when the incision blade assembly 16 is in a retracted position as shown in FIG. 1. The upper end 62 of the bore 56 has a reduced diameter to define a spring chamber 64. A spring 66 is coiled about the post 54 with the upper and lower ends thereof in abutting engagement with the shoulder 68 formed by the reduced diameter portion 62 and the enlarged lower end 58 of the post 54, respectively. When the blade assembly 16 is in the position shown in FIG. 1, the spring 66 is in a compressed state.

The upper end 69 of the post 54 extends through a slide chamber 70 and a hole 71 formed in the housing above the slide chamber 70. A slide 72 has a transverse portion 73 and a portion extending upwardly through a slot 74 formed in the upper end of the housing. The transverse portion 73 of the slide 72 has a slotted opening 75 forming spaced arm members 76, 77. The slotted opening 75 extends inwardly to a circular aperture 80 having a diameter greater than the outer diameter of the upper end 69 of the post 54. The arm members 76, 77 are spaced apart a distance less than the outer diameter of the upper end 69 of the post 54 such that the arm members 76, 77 are slidably seated in recesses 81, 82 formed on opposite sides of the upper portion of the post 54. When the arm members 76, 77 are seated in the recesses 81, 82 as shown in FIGS. 1 and 2, the incision blade assembly 16 is retained in the position shown in FIG. 1 with the spring 66 in a compressed state.

An enlarged chamber 83 is provided above the blade aperture 31 of the housing to provide a blood reservoir in the event there is an initial surge of blood when the skin is punctured by the blade 20. By providing the chamber 83 to receive a possible initial surge of blood, the possibility of increasing the incision outside of desired dimensions as a result of such a surge of blood seeking a flow path around the lower end of the device 10 is minimized.

In the specific embodiment shown in the figures, the blade 20 has a pair of spaced cutting edges 84, 85 for making two spaced incisions in a patient, and thereby provide an opportunity to average the bleeding times of in incisions. Obviously, the blade can have one cutting edge or more than two cutting edges.

The lower end of the device 10 is shaped to minimize the portion of the device 10 in contact with the skin and to depress and stretch the skin such that reproducible skin punctures are provided. Specifically, the blade aperture 31 is formed in a portion of the device 10 defined by beveled side walls 86, 87 and beveled front and rear walls 88, 89.

The device 10 is assembled as shown in FIGS. 1, 2 and 4 with the blade holder 18 functioning to retract the blade 20 inwardly from the blade aperture 31 against the bias of the spring 66. The slide 72 is in releaseable engagement with the upper end of the post 54 of the blade holder 18 to maintain the blade 20 in a retracted position until the device 10 is ready for use. The slide 72 is manually operable to move to the right as viewed in FIG. 1 in the slide chamber 70, until the circular aperture 80 is positioned about the upper end 69 of the post 54. At this time, the slide 72 is disengaged from the blade holder 18, and the blade holder 18 rapidly moves downwardly under the bias of the spring 66. The blade holder 18 is guided downwardly by the rails 34–40 and the grooved recesses 42–48 until the lower surface 90 of the blade holder wall 32 abuts the bottom surface 91 of the hollowed portions of the side walls 50, 52. At this time, the cutting edges 84, 85 are positioned a predetermined distance outwardly from the blade aperture 31 to provide incisions of predetermined dimensions in the skin of a patient. For example, each one of the cutting edges 84, 85 suitably can be 6 mm in length.

With the exception of the blade 20, all of the components of the device 10 are formed from plastic material, and the components are permanently assembled by bonding the side walls 12, 14 together to provide a relatively inexpensive disposable device. Further, once the blade holder 18 is released from the slide 72, the blade holder 18 cannot be retrieved to again retract the incision blade assembly 16 for reuse.

A device constructed in accordance with the specific embodiment shown in the figures was tested on 27 normal individuals and gave normal bleeding times of 3.91 minutes and a range of 2 to 6 minutes. Varying the pressure placed on the arm by the device did not affect the bleeding times.

What is claimed is:

1. A device for testing the bleeding time of a human subject comprising:
   a. a housing including a blade aperture at a distal end thereof adapted to be positioned in abutting engagement with the skin of said subject:
   b. a blade member in said housing, said blade member having at least one linear cutting edge of selected length disposed at a right angle to the direction of movement of said blade member and in registration with said aperture;
   c. a spring member in said housing for urging said blade member in a direction toward said aperture and perpendicular to said edge;
   d. means in said housing and connected to said blade member for holding said blade member, said holding means being in slideable engagement with an internal surface of said housing for aligning said blade member with said aperture and having a surface thereon against which said spring member acts;
   e. means engaging said housing for releasable retaining said holding means to maintain said edge internally of said housing against the bias of said spring member until the device is ready for use;
   f. said retaining means being manually operable to irretrievably free said holding means, said holding means and said blade member being moveable under the bias of said spring member to position said at least one cutting edge a predetermined distance outwardly from said blade aperture; and
   g. stop means on said housing against which said holding means abuts when said blade member is at said predetermined distance.

2. The device of claim 1 wherein said blade member includes at least two spaced linear coplanar cutting edges, said cutting edges being simultaneously positioned outwardly from said blade aperture.

3. The device of claim 2 wherein the at least two cutting edges are formed on one blade member.

4. The device of claim 1 wherein said blade aperture is formed in a portion of said housing having reduced dimensions to minimize the surface area of said housing in contact with the skin of the subject.

5. The device of claim 1 wherein said blade aperture is elongated, and wherein said housing is beveled away from said aperture to minimize the surface area of said housing in contact with the skin of the subject.

6. The device of claim 5 wherein a chamber having a cross-sectional area greater than the area of said blade aperture is located above said aperture.

7. The device of claim 1 wherein said holding means is slideably engaged and aligned by two opposing internal surfaces of said housing, said surface against which said spring member acts is located on a member upwardly depending from said holding means and axially aligned with said aperture, and said spring member is a helically wound spring axially mounted on said, said spring member acting against said holding means surface and said housing to urge said blade member toward contact with said skin.

8. The device of claim 7 wherein said depending member is a post and said retaining means includes a pair of spaced arms for releasably engaging an upper portion of said post.

9. The device of claim 8 wherein a distal upper end of said post has a predetermined diameter, and wherein said retaining means has an opening having a diameter greater than said predetermined diameter; said arms engaging said upper end of said post therebetween to maintain said blade holding means in said retracted position, and said slide member being movable with respect to said post to locate said opening about said upper end and thereby disengage said upper end.

10. The device of claim 9 wherein said slide member is perpendicularly movable with respect to said post.

11. The device of claim 10 wherein each one of said arms is seated in a recess on opposite sides of said upper post end.

12. The device of claim 9 wherein each one of said arms is seated in a recess on opposite sides of said upper post end.

13. A method of testing the bleeding time of a human subject comprising:

a. positioning a linear cutting edge in a plane parallel to the skin of the subject;
b. moving the edge to puncture the skin of the subject in a direction normal to the plane of the edge; and
c. measuring the bleeding time of the puncture.

14. The method of claim 13 including the steps of positioning at least two coplanar linear cutting edges parallel to the skin, puncturing the skin with the two edges simultaneously and measuring and averaging the bleeding time of each puncture.

* * * * *